(12) United States Patent
Germain

(10) Patent No.: US 9,676,873 B2
(45) Date of Patent: Jun. 13, 2017

(54) BLEACHED DEXTRIN AND METHODS OF FORMING THE SAME

(71) Applicant: Archer Daniels Midland Company, Decatur, IL (US)

(72) Inventor: Normand Germain, Quebec (CA)

(73) Assignee: Archer Daniels Midland Company, Decatur, IL (US)

(*) Notice: Subject to any disclaimer, the term of this patent is extended or adjusted under 35 U.S.C. 154(b) by 123 days.

(21) Appl. No.: 14/657,031

(22) Filed: Mar. 13, 2015

(65) Prior Publication Data

US 2015/0183889 A1 Jul. 2, 2015

Related U.S. Application Data

(63) Continuation of application No. 13/264,418, filed as application No. PCT/US2010/030673 on Apr. 12, 2010, now Pat. No. 8,999,066.

(60) Provisional application No. 61/170,241, filed on Apr. 17, 2009.

(51) Int. Cl.

| | | |
|---|---|---|
| *C08B 37/00* | (2006.01) | |
| *C08B 30/18* | (2006.01) | |
| *A61K 31/733* | (2006.01) | |
| *A61K 31/718* | (2006.01) | |
| *C08B 15/02* | (2006.01) | |
| *C08B 31/18* | (2006.01) | |
| *C08B 37/16* | (2006.01) | |
| *A23L 29/30* | (2016.01) | |

(52) U.S. Cl.
CPC ............ *C08B 30/18* (2013.01); *A23L 29/35* (2016.08); *A61K 31/718* (2013.01); *A61K 31/733* (2013.01); *C08B 15/02* (2013.01); *C08B 31/18* (2013.01); *C08B 37/0009* (2013.01); *C08B 37/0012* (2013.01); *C08B 37/0054* (2013.01)

(58) Field of Classification Search
CPC .. C08B 37/0009; C08B 37/0012; A23L 29/35
See application file for complete search history.

(56) References Cited

U.S. PATENT DOCUMENTS

| | | | | |
|---|---|---|---|---|
| 4,622,233 | A * | 11/1986 | Torres | A23C 9/1544 426/3 |
| 8,999,066 | B2 * | 4/2015 | Germain | C08B 15/02 127/40 |
| 2003/0096055 | A1 * | 5/2003 | Fuertes | C08B 30/18 426/661 |

OTHER PUBLICATIONS

US 4,684,410, 08/1987, Morehouse et al. (withdrawn)*
Dias et al, Oxidation of Fermented Cassava Starch Using Hydrogen Peroxide, Carbohydrate Polymers, 86 (2011) pp. 195-191.*

* cited by examiner

*Primary Examiner* — David M Brunsman
(74) *Attorney, Agent, or Firm* — Alexandra Lakshmanan

(57) ABSTRACT

Bleached dextrin compositions, methods of forming the same, and products formed therefrom. The composition comprises a dextrin-based composition or slurry, a caustic agent, and an oxidant. The caustic agent may include sodium hydroxide. The oxidant may include hydrogen peroxide.

20 Claims, 1 Drawing Sheet

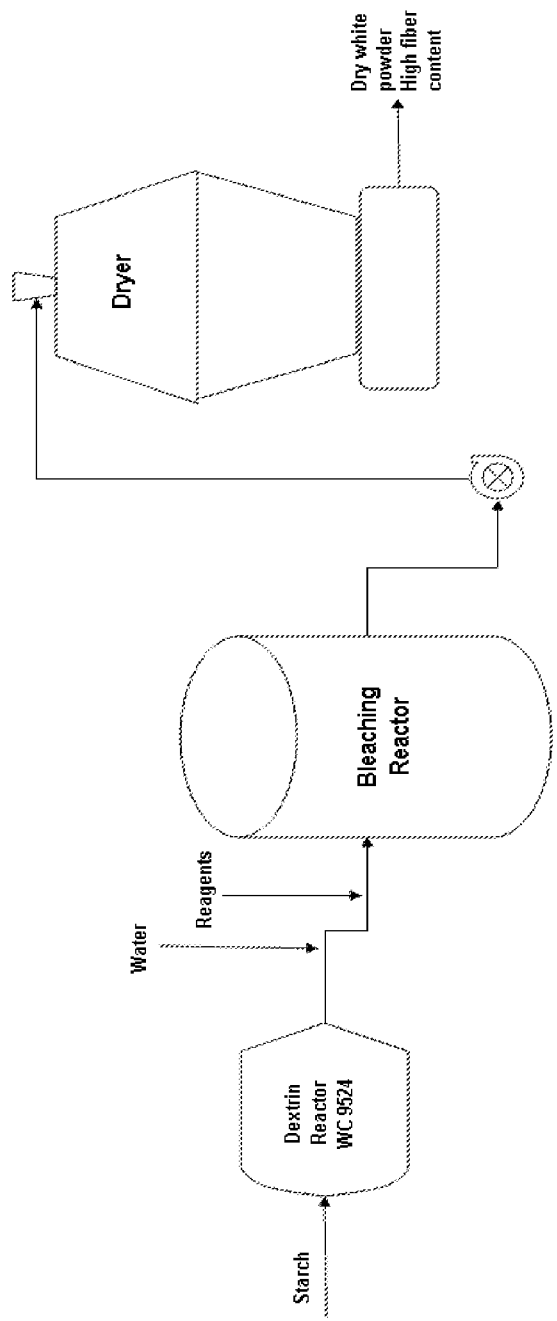

BLEACHED DEXTRIN AND METHODS OF FORMING THE SAME

CROSS-REFERENCE TO RELATED APPLICATIONS

This application is a continuation of application Ser. No. 13/264,418, filed Oct. 14, 2011, now U.S. Pat. No. 8,999,066, which itself is a national stage entry of International Application No. PCT/US10/030673, filed Apr. 12, 2010, which itself claims priority to U.S. Provisional Patent Application No. 61/170,241, filed Apr. 17, 2009, each of the contents of the entirety of which are incorporated by this reference.

TECHNICAL FIELD

The present disclosure relates to bleached dextrin and methods of forming the same.

BACKGROUND

Starch is a naturally occurring polymer made up of anhydroglucose units and is obtained by processing plant materials. The plant materials from which starch is derived include, but are not limited to, corn, wheat, potato, cassava, and rice. Of these plant materials, corn is one of the most commonly used sources for starch in North America.

Starch is composed of two main components: amylose and amylopectin. Amylose is a linear polymer of glucose linked with mostly α(1→4) glycosidic bonds. Amylopectin is a branched polymer of glucose linked with both α(1→4) and α(1→6) glycosidic bonds.

A digestion-resistant carbohydrate is a carbohydrate that resists digestion in the human body. Such digestion-resistant carbohydrates can be prepared by heat-treating starch at a high temperature in a process called dextrinization.

Dextrinization rearranges the molecular structure of starch to form indigestible branched structures. Through dextrinization, a portion of the normal α(1→4) glycosidic bonds in starch are converted to random (1→4), (1→3) and (1→2)-alpha or beta bonds. These chemical changes are described in "Modified Starches: Properties and Uses", O. B. Wurzburg, CRC Press, Inc. 1986, pp. 33-34. The human digestive system can only effectively digest α(1→4) bonds and not the α(1→3) and α(1→2) glycosidic bonds. Thus, digestion-resistant carbohydrate remains undigested in the small intestine.

In addition to digestion-resistant carbohydrate, dextrins are also produced as intermediate products through the process of dextrinization. Dextrins are a group of low molecular weight carbohydrates that have the same general formula as starch, but are smaller and less complex.

Dextrins may be categorized as either pyrodextrins or maltodextrins according to the method of dextrinization. For example, pyrodextrins are dextrins that are prepared from acid hydrolysis and heat treatment. Maltodextrins are either dextrins that are prepared from acid hydrolysis followed by enzymatic hydrolysis of the acid hydrolysate or dextrins that are prepared from enzymatic hydrolysis during heating.

Dextrins are used for numerous industrial applications. Examples of relevant manufacturing areas include, but are not limited to, the adhesive industry, the paper industry, the pharmaceutical industry, the mining industry, the food industry, and the textile industry. More specifically, dextrins can be used in water soluble glues, printing inks, food products, substitutes for lactose, and adhesives (e.g. for postage stamps, envelopes, and wallpapers). In addition, some indigestible dextrins are used in fiber supplements. For example, dextrin is used to make digestion-resistant maltodextrin (e.g., Fibersol-2®, a registered trademark of Matsutani Chemical Industry Co., Ltd., Itami-shi Hyogo-ken, JAPAN).

In preparation of digestion-resistant carbohydrate in dextrin (indigestible dextrin), the degree of dextrinization depends for example, on the temperature employed, the speed of heating, the time of holding the starch at the selected temperature, and the type and amount of acid or catalyst that is used. This also results in the development of color due to carmelization reactions. Carmelization reactions are a diverse group of dehydration, fragmentation, and polymerization reactions whose reaction rates are dependent on temperature and pH (See, "Sugar Chemistry", R. S. Shallenberger and G. G. Birch, AVI, 1975, pp. 167-177).

As a result of the dextrinization and carmelization reactions, dextrins can be distinguished according to their physical properties including, but not limited to, color and solubility in water. Types of dextrins include white dextrins, yellow dextrins, and British gums.

White dextrins may be prepared by heating starch at 79° C. to 121° C. in the presence of acid catalyst for 3 to 8 hours. Under these conditions, the starch is hydrolyzed, whereby the long chain of glucose units of the starch molecule is reduced considerably. White dextrins generally have a limited cold water solubility and a limited stability of solution. After cooling, a cooked, aqueous solution of white dextrins soon sets to a paste.

Yellow dextrins are prepared by heating starch at 120° C. to 220° C., with the addition of acid catalyst for 6 to 8 hours. As a result of a transglucosidation reaction, yellow dextrins have more of a branched structure compared to white dextrins. A transglucosidation reaction is considered to be a recombination of fragments resulting from the hydrolysis with free hydroxyl groups to produce branched structures. The branching increases as the heat conversions are carried out at higher temperatures, or as the reaction time increases. Furthermore, the yellow dextrins have a higher cold water solubility as well as a more hydrophilic character relative to white dextrins.

British gums are prepared by applying heat at a relatively high pH in comparison with the white and yellow dextrins. For example, British gums are prepared by heating starch at 135° C. to 218° C. in the absence of acid catalyst for 3 to 8 hours. As a result of the high temperatures employed, British gums are considerably darker in color than white dextrins.

Improvements in the standard of living have resulted in an increased interest in health and improved eating habits which, among other factors, have resulted in a lengthened average life span. Attention has therefore been directed to dietary fibers and oligosaccharides to enhance the functions of foods and livestock feeds, as these materials are known to alleviate constipation and other desired biological regulatory functions. Indigestible substances, like indigestible dextrins, exhibit various modes of behavior on the digestive tracts, producing physiological effects on the living body. First, in the upper digestive tract, indigestible dextrins slow the transport of food and delay the absorption of nutrients. Delayed absorption of sugar, for example, suppresses the rise in blood sugar value, consequently lowering insulin requirements. Further, excretion of bile is promoted, diminishing the sterol group in the body thereby lowering the cholesterol level in the serum. Other physiological effects through the endocrine system are also reported.

Indigestible substances are not digested or absorbed by the digestive tract, including the small intestine and eventually reach the large intestine. On reaching the large intestine, oligosaccharides, dietary fibers and indigestible dextrins are partly acted on by enterobacteria yielding short-chain fatty acids, intestinal gases, vitamins, etc. Acidification of the intestinal environment by the short-chain fatty acids condition the intestine. It has been reported that when these short chain fatty acids are metabolized, they provide energy and inhibit the synthesis of cholesterol. Therefore, indigestible substances are necessary in obtaining many desirable physiological effects.

As mentioned herein, digestion-resistant carbohydrate in dextrin (indigestible dextrin) is an important part of the human diet and provides several health benefits. However, the development of indigestible dextrin typically occurs contemporaneously with color development as the dextrinization reaction progresses. As starch is heated under altered conditions to obtain a higher indigestible starch content, the product increases the amount of colored substance, therefore, requiring purification.

In addition to high indigestible content, color is also often a major consideration in choosing a dextrin appropriate for a particular industrial application. Thus, the method of treatment that is used to produce indigestible dextrin depends directly on the intended application. For instance, a lack of brown color may be desirable in choosing a dextrin for use in paper adhesives, pharmaceutical, or food products, while brown dextrins may have more desirable tack and solubility characteristics.

Often times, it is preferable that the finished indigestible dextrin product be almost colorless in solution due to its application in the food industry. In the majority of cases, any color developed in the dextrinization process is not desirable in the final product and is largely removed through subsequent, and costly, decolorization steps. In order to minimize the costs associated with color removal, dextrins with minimal color development would be advantageous.

Thus, there is a need for bleached dextrins lacking in color with high indigestible starch content and methods of producing the same. The object is to manufacture a dextrin with the greatest degree of digestion-resistant carbohydrate possible while minimizing objectionable color formation.

SUMMARY OF THE INVENTION

Disclosed herein are various non-limiting embodiments generally related to methods of forming bleached dextrins comprising dextrin-based compositions, including, but not limited to, dextrin pastes, dextrin slurries, and any combination thereof.

In one embodiment, the present disclosure provides a method of forming a bleached dextrin comprising combining a dextrin-based composition with a moisture content of 20% by weight or lower with a caustic agent and an oxidant to form a mixture. The mixture may be heated at an optimal temperature for a period of time and dried to form the bleached dextrin.

In another embodiment, the present disclosure provides a method of forming a bleached dextrin comprising forming a dextrin-based slurry and combining the dextrin-based slurry with sodium hydroxide and hydrogen peroxide to form a mixture. The mixture may be heated for a period of time, dried to form the bleached dextrin, and ground.

In another embodiment, the present disclosure provides a method of forming a bleached dextrin comprising hydrating 0.3 to 3 parts powdered dextrin with 1 to 5 parts water by weight to form a dextrin-based composition. The dextrin-based composition may be combined with sodium hydroxide to form a first mixture with a pH of 6 to 10. Hydrogen peroxide may be combined with the first mixture to form a second mixture. The second mixture may be incubated between 20° C. and 50° C. for 0 to 2 hours and dried to form the bleached dextrin.

It should be understood that this invention is not limited to the embodiments disclosed in this Summary, and it is intended to cover modifications that are within the spirit and scope of the invention, as defined by the claims.

DESCRIPTION OF THE DRAWINGS

FIG. 1 is a diagram of the manufacturing method for bleaching food grade dextrin with high fiber content.

DETAILED DESCRIPTION

Other than in the examples herein, or unless otherwise expressly specified, all of the numerical ranges, amounts, values and percentages, such as those for amounts of materials, elemental contents, times and temperatures of reaction, ratios of amounts, and others, in the following portion of the specification and attached claims may be read as if prefaced by the word "about" even though the term "about" may not expressly appear with the value, amount, or range. Accordingly, unless indicated to the contrary, the numerical parameters set forth in the following specification and claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains error necessarily resulting from the standard deviation found in its underlying respective testing measurements. Furthermore, when numerical ranges are set forth herein, these ranges are inclusive of the recited range end points (i.e., end points may be used). When percentages by weight are used herein, the numerical values reported are relative to the total weight.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10. The terms "one," "a," or "an" as used herein are intended to include "at least one" or "one or more," unless otherwise indicated.

Any patent, publication, or other disclosure material, in whole or in part, that is identified herein is incorporated by reference herein in its entirety, but is incorporated herein only to the extent that the incorporated material does not conflict with existing definitions, statements, or other disclosure material set forth in this disclosure. As such, and to the extent necessary, the disclosure as explicitly set forth herein supersedes any conflicting material said to be incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The present disclosure provides various features and aspects of the exemplary embodiments provided herein. It is understood, however, that the present disclosure embraces numerous alternative embodiments, which may be accomplished by combining any of the different features, aspects, and embodiments described herein in any combination that one of ordinary skill in the art may find useful.

Various non-limiting embodiments of the present disclosure are directed to methods of forming a bleached dextrin comprising combining a dextrin-based composition with a caustic agent, such as sodium hydroxide, and an oxidant, such as hydrogen peroxide, to form a mixture. As used herein, the term "mixture" refers to any combination of at least two components and includes, for example, blends, dispersions, solutions, emulsions, suspensions, and combinations of any thereof. The mixture may be heated for a period of time and dried to form bleached dextrin.

In the present disclosure, various dextrins may be employed in dextrin-based compositions set forth herein. As used herein, the term "dextrin-based composition" refers to a composition containing 40%, by weight dextrin of any color or a mixture of one or more thereof, with a moisture content of 20% or lower in any physical form such as for example a paste, a slurry, or any combination thereof. For example, dextrins that vary in color from white to dark brown may be employed in the dextrin-based composition set forth herein.

Dextrins are a group of low molecular weight carbohydrates produced as intermediate products in the hydrolysis and depolymerization of starch using a dextrin reactor. Any suitable reactor may be employed in the dextrinization process of the present disclosure. For example, a NOREDUX cooker type F/11, commercially available from NOREDUX, may be employed. The term "dextrin" refers to any one of a number of oligo-D-glucose compounds having the same general formula as starch, but is smaller and less complex. Often times dextrins may be divided into two distinct groups: pyrodextrins and maltodextrins. Pyrodextrins are the product of the dextrinization of starch using heat and acid. The large scale production of pyrodextrins may be used for non-food related applications. Maltodextrins are the product of the dextrinization of starch using enzymes coupled with acid hydrolysis or heating. The large scale production of maltodextrins may be used for food related applications or products.

Dextrins may be classified according to several different criteria. First, dextrins may be classified according to the source of the starch from which they are derived. For example, dextrins may be derived from corn starch, wheat starch, potato starch, cassava starch, rice starch, sorghum and any combination thereof. As used herein, the term "starch" refers to a complex carbohydrate found chiefly in seeds, fruits, tubers, roots and stem pith of plants, notably in corn, potatoes, wheat, and rice. Second, dextrins may also be classified according to the iodine affinity of the finished dextrins. For example, some dextrins react with iodine resulting in a reddish-brown color, a blue color, or no color. Also, dextrins may be classified according to the method of treatment that is used to depolymerize starch to form the dextrins. Examples of treatments that are used to depolymerize starch include, but are not limited to heat, acid, oxidizing agents, ultraviolet irradiation, gamma irradiation under acidic conditions, phosphorous pentachloride, acetyl bromide, and enzymes. Various types of dextrins are known, including white dextrins, yellow dextrins, and British gums.

In certain embodiments of the present disclosure, the dextrin-based composition may comprise white dextrins. White dextrins (color neutral) may be prepared by combining starch with a large amount of added catalyst (e.g., hydrochloric acid), and heating mildly, for instance at 79° C. to 121° C., for a short time (3 to 8 hours). The resulting white dextrins may be white or nearly white, may have very limited solubility in water, and may retain a number of the characteristics of the original starch paste. White dextrins may form an adhesive paste when mixed with water and may be used in the manufacture of paper products, because it is white and does not cause the paper to wrinkle.

White dextrins are only slightly treated, while more severe treatments (e.g., increased heat, time, and/or chemical concentration) produce dextrin products of increasingly dark color. For instance, white dextrins may be produced by gentle roasting (i.e., heating below 150° C.) of acidified starch, while yellow dextrins may be made by stronger roasting of acidified starch. Effectively, white dextrins will become yellow dextrins with continued treatment.

In certain embodiments of the present disclosure, the dextrin-based composition may comprise yellow dextrins. In other embodiments, the dextrin-based composition may contain a sufficient amount of yellow dextrins, such that the dextrin-based composition may be yellow in color. Yellow dextrins may be formed when lower acid or catalyst levels are used with higher temperatures of conversion (e.g., 120° C. to 220° C.) for longer periods of time (6 to 8 hours), relative to white dextrins. Yellow dextrins may be soluble in water, and may form solutions that are light yellow to brown in color, and may have a relatively low viscosity.

In certain embodiments of the present disclosure, the dextrin-based composition may comprise British gums. British gums may be made by heating the starch by itself, or may be combined with small amounts of alkaline buffer salts, at 135° C. to 218° C. The final product may be brown, ranging from light to dark brown. British gums may be soluble in water. In other embodiments, the dextrin-based composition may contain a sufficient amount of British gums such that the dextrin-based composition may be one of light brown, beige, or dark brown in color.

In certain embodiments, the dextrin-based composition may be in a form selected from the group consisting of a slurry, a paste, or any combination thereof. In certain embodiments, the dextrin-based composition may be a homogenous slurry of 5 to 55% solids. In other embodiments, the dextrin-based composition may be a paste with greater than 55% solids. The term "dextrin-based slurry," as used herein, refers to a suspension of dextrin particles in a liquid medium. In certain embodiments of the present disclosure, the dextrin-based composition may comprise water and a high fiber dextrin. As used herein, "high fiber" refers to higher than 25% fiber. The high fiber dextrin may be various dextrins, such as those selected from the group consisting of starch dextrin, cyclodextrins, inulin, hydrogenated indigestible dextrins, hydrogenated starch hydrolysates, highly branched maltodextrins, cellulose, and combinations of any thereof. In certain embodiments, the high fiber dextrin may include Fibersol-2®.

In certain embodiments of the present disclosure, the dextrin-based composition may have a moisture content of 20% by weight or lower. In other embodiments of the present disclosure, the dextrin-based composition may have a moisture content of 30% by weight or lower. In still other embodiments of the present disclosure, the dextrin-based composition may have a moisture content of 40% by weight or lower. In other embodiments, the dextrin-based composition may have a moisture content of 35% to 85% by weight.

The present disclosure provides methods of forming bleached dextrin from the dextrin-based compositions, set forth herein. Various embodiments of the present disclosure are directed to methods of forming a bleached dextrin comprising hydrating the powdered dextrin. For example, 0.3 to 3 parts powered dextrin may be hydrated with 1 to 5 parts water by weight to form a dextrin-based composition. In certain embodiments, the dextrin-based composition may be formed by hydrating 1 to 100 parts powdered dextrin with 1 to 50 parts water by weight. In other embodiments, the dextrin-based composition may be formed by hydrating 1 to 10 parts powdered dextrin with 1 to 10 parts water by weight.

In certain embodiments, the method of forming bleached dextrin may include forming a mixture comprising the dextrin-based composition, as set forth herein, a caustic agent, and an oxidant.

Various caustic agents known to those of ordinary skill in the art may be employed in embodiments of the present disclosure. Examples of suitable caustic agents include, but are not limited to, sodium hydroxide, calcium carbonate, sodium carbonate, trisodium phosphate, and lime. The caustic agent may be added in various states or phases including, but not limited to, solids and liquids. Any suitable concentration of the caustic agent may be employed when added to the dextrin-based composition in various amounts of up to 10% by weight on a dextrin dry basis. For example, in certain embodiments of the present disclosure, a caustic agent, such as sodium hydroxide from 0.1 to 100% by weight, may be added to a dextrin-based composition in an amount ranging from 0.01% to 10% by weight on dextrin dry basis. In other embodiments, a caustic agent may be added to the dextrin-based composition in an amount ranging from 0.1% to 3% by weight on a dry basis. In certain embodiments, the caustic agent may be added dry or under a solution.

In certain embodiments the caustic agent such as sodium hydroxide may be combined with the dextrin-based composition to form a first mixture at a pH ranging from 1 to 10, in other embodiments, a pH ranging from 4 to 10, in other embodiments, a pH ranging from 6 to 10 and in still other embodiments may be combined at a pH ranging from 8 to 10. As used herein, the term "first mixture" refers to a mixture comprising a dextrin-based composition combined with a caustic agent. The caustic agent is added before the oxidant to stabilize and control the pH of the first mixture.

In certain embodiments of the present disclosure, methods of forming bleached dextrin may include adding an oxidant to the dextrin-based composition to form a second mixture. As used herein, the term "second mixture" refers to a mixture comprising a dextrin-based composition combined with a caustic agent and oxidant. Various oxidants known to those of ordinary skill in the art may be employed in embodiments of the present disclosure. Examples of suitable oxidants include, but are not limited to, hydrogen peroxide and benzoyl peroxide. Any suitable concentration of the oxidant may be employed when added to the dextrin-based composition in amounts of up to 10% by weight on a dextrin dry basis. For example, in certain embodiments, an oxidant such as hydrogen peroxide may be added to the dextrin-based composition in an amount ranging from 0.1% to 10% by weight on a dry basis. In other embodiments, oxidants such as hydrogen peroxide at a concentration of 0.1% to 70% may be added to the dextrin-based composition in an amount ranging from 3% to 15% by weight on a dextrin dry basis. In other embodiments, a concentration of 25% to 70% hydrogen peroxide may be used.

Although the time of addition of the oxidant may vary, in certain embodiments, the oxidant may be added to the first mixture for a time ranging from 5 to 120 minutes, in other embodiments for 5 to 60 minutes, in other embodiments for 5 to 45 minutes, in some embodiments for 5 to 30 minutes, in still other embodiments for 5 to 20 minutes, and in other embodiments for 10 to 20 minutes. In certain embodiments, the oxidant may be added to the first mixture under a controlled pH with the caustic agent, such as sodium hydroxide. In certain embodiments, the pH may be controlled for 5 to 60 minutes, in some embodiments for 5 to 45 minutes, in other embodiments for 5 to 30 minutes, in other embodiments for 5 to 20 minutes, and in still other embodiments for 10 to 20 minutes to complete the reaction.

The mixture of dextrin-based composition, caustic agent and oxidant may be combined at a certain pH and/or may be heated at an elevated temperature for a certain period of time in a bleaching reactor as illustrated in FIG. 1. As used herein, the phrase "elevated temperature" is meant to include those temperatures above 30° C., and in certain embodiments above 40° C. Any suitable reactor may be employed in the process of the present disclosure. For example, a Fiberglass mixing tank with agitator commercially available from MILLER PLASTIC PRODUCTS may be employed. In certain embodiments, the second mixture may have a pH ranging from 6 to 10. In certain embodiments, the mixture may be heated to a temperature ranging from 10° C. to 80° C. for a period of time ranging from 10 to 360 minutes. In other embodiments, the mixture may be heated to a temperature ranging from 20° C. to 50° C. for a period of time ranging from 20 to 120 minutes. In certain embodiments, the second mixture may be incubated for 45 minutes at a temperature ranging from 20° C. to 50° C. In other embodiments, the second mixture may be incubated at a temperature ranging from 20° C. to 50° C. for 60 minutes, in some embodiments for 30 minutes, and in other embodiments for 15 minutes.

In other embodiments of the present disclosure, an enzyme may be added to remove excess hydrogen peroxide before drying the mixture. Examples of enzymes that may be used include, but are not limited to, catalase and peroxidase. In other embodiments, a dosage of 100 ppm or more of enzyme may be added to the mixture without affecting the final product.

After heating the mixture for a period of time, the mixture may be dried to form the bleached dextrin in a dryer as illustrated in FIG. 1. In certain embodiments, the heating and drying may be performed simultaneously. Any suitable dryer may be employed in the embodiments of the present disclosure. For example, a spray dryer commercially available from Barr & Murphy may be employed. As used herein, "spray drying" refers to a commonly used method of drying a liquid feed (spray) through a hot gas. Typically, the hot gas is air. In certain embodiments, the mixture may be dried at a temperature ranging from 40° C. to 500° C. for a period of time ranging from 1 to 120 minutes. In other embodiments, the mixture may be dried at a temperature ranging from 60° C. to 250° C. for a period of time ranging from 1 to 120 minutes.

In certain embodiments, the mixture may be ground into suitable size particles. Any suitable grinder may be employed in the embodiments of the present disclosure. For example, a grinder commercially available from Palmann may be employed. The mixture may be ground into any suitable sized particles, such as those particles ranging from 30 to 500 mesh (600 to 25 microns). In certain embodiments, the ground particles may be 100% finer than 30 mesh (600 microns). The average particle size can be measured according to known techniques. For example, the average particle size of such particles may be measured using a laser diffraction particle size analyzer, commercially available from Beckman Coulter, Inc., Fullerton, Calif., which is a particle size instrument to measure the size of the particles and assumes the particle has a spherical shape, i.e., the "particle size" refers to the smallest sphere that will completely enclose the particle. Particle size can also be measured by USA Standard Sieve Method ASTME-II specification.

In certain embodiments, the bleached dextrin product may have the same fiber content compared to the starting dextrin material. In other embodiments, the bleached dextrin product may have had slightly higher fiber content compared to the starting dextrin material. In certain embodiments, the fiber content may be between 25% by weight to 60% by weight.

In certain embodiments, the bleached dextrin product produced by the methods described herein may be very white or slightly white in color. CIE lab is a conventional color model that is used to describe all the colors that are visible to the human eye. This model consists of three basic coordinates: coordinates that represent the lightness of color; coordinates positioned between magenta and green; and coordinates between yellow and blue.

In operation, there are two tests that measure color. The first test is a whiteness meter and is run on dry dextrin samples. An example of a whiteness meter is a Kett Electric Laboratory Whiteness meter, model C-1, with a range of 0 to 100, where 0 represents the darkest and 100 represents the whitest points on the scale. The second test employs a spectrophotometer to measure the color of a dextrin sample dissolved in water in the form of a slurry at ten percent dry solids. In the second test, higher levels of absorbance indicate a more colored product. The absorbance is monitored by a spectrophotometer at wavelengths of 420 and 720 nm, with the difference being multiplied by ten and recorded as the color.

When a process to manufacture digestion-resistant carbohydrate is designed, the design parameters take into account both a whiteness value and an absorbance color value of the dextrin because the decolorization steps, such as carbon treatment, can only treat a certain amount of color bodies before recharging. In order to keep costs at economic levels, the dextrinized starch must not be too colored. For example, it has been found that by maintaining a whiteness value of 65 and an absorbance color value of 20 or lower, the subsequent decolorization steps result in an end product that is economically viable.

The object of the dextrinization process is to produce a dextrin containing the highest yield of digestion-resistant carbohydrate possible while maintaining a whiteness value above 65 and a spectrophotometer color below 20. Although other whiteness and absorbance color targets can be used, these targets require either more or less equipment to remove the color depending on whether it is less colored (less equipment and materials) or more colored (additional equipment and materials).

In certain embodiments, the bleached dextrin may have a whiteness level ranging from 90 to 100% based on CIE Lab model. In other embodiments, the bleached dextrin may have a whiteness level ranging from 94 to 100% based on CIE Lab model. In other embodiments, the bleached dextrin may have a whiteness level ranging from 80 to 100% based on CIE Lab model.

Bleached dextrins may be made by the methods described above and may be used for numerous industrial applications. Some examples of relevant industries include, but are not limited to the adhesive industry, the paper industry, the pharmaceutical industry, the mining industry, the textile industry, and the food industry. For example, a food product may comprise bleached dextrin made by the method described above. In certain embodiments, the food product may be selected from the group consisting of baked goods, snack foods, pie fillings, and beverages. In other embodiments, the food products may include teas, cola drinks, juices, sports drinks, milk shakes, ice cream, fermented skimmed milk hard yogurt, coffee whitener powder, candy, chewing gum, sweet chocolate, custard cream, jellies and jams, including orange jelly, strawberry jam, apple jam, bean jam, and sweet jelly of beans, cereals, pastas, breads, donuts, wheat flower replacer, cookies, cakes, pies, soups, curries, stews, non-oil dressing (MIRACLE WHIP® type), mayonnaise, peanut butter, cheese powder, cream cheese, sauces, beef and pork sausage, corned beef, hamburger steak, hamburger patty, liver paste, pizza, omelets, filing of meat pie, filling of Chinese dumplings, kamaboko, black berry liquor, dog food, cat food, pig and cattle feed, feed for broiler poultry and feed for laboratory rodents. Dextrin may also be used to make digestion resistant maltodextrin, such as Fibersol-2®. Examples of non-food industrial uses of the dextrins provided herein may include the manufacture of corrugated cardboard, plywood, wallpaper, and the remoistening gums and related adhesives found on postage stamps and envelopes.

For uses such as postage stamps, envelope flaps and wallpaper, and pharmaceutical and food products, whiteness (i.e., lack of color) may be an important consideration in the choice of dextrin to be used. In postage stamps, envelopes, and pharmaceutical products, lack of taste may also be an important factor. For example, bleached dextrin has a reduced burnt notes taste.

According to other embodiments of the present disclosure, any of the methods described herein may further include the steps of placing the bleached dextrin composition in a container which may be configured for shipping. The methods may further comprise associating indicia with the container, such as, for example, placing graphical, written, or numerical indicia on the container. The indicia may be capable of describing the contents of the container, designating the producer of the contents, and/or directing an end user, such as, for example, a food manufacturer, on how to use the composition in the production of a food product. According to other embodiments, the methods may further comprise shipping the container containing the bleached dextrin composition. Any conventional method of shipping may be used, such as, for example, shipping by truck, train, ship, plane, or any combinations thereof.

The present invention may be further understood by reference to the following examples. The following examples are merely illustrative of the invention and are not intended to be limiting. Unless otherwise indicated, all parts are by weight.

EXAMPLES

Example 1

Ten grams (10 g) of WC 9524 (ADM Canadian Plant commercial product), canary dextrin, made of wheat starch was mixed with a 3% caustic solution (sodium hydroxide) in a beaker to form a paste. The paste was mixed manually with a spatula to homogenize the mixture and obtain a smooth paste.

Sodium hydroxide (3%) solution was mixed until the color of dextrin became brown. The brown color is an indication of a pH close to 8.5 or higher. The pH was stabilized by continuous mixing the paste before adding the hydrogen peroxide reagent. The exact dosage of hydrogen peroxide was not measured when added to the paste in this first experiment. Instead, hydrogen peroxide was merely added to verify whether bleaching occurred. After 15 minutes of continuous mixing, the paste-like mixture became white in color. The paste-like mixture was then dried in an oven at 60° C. to produce a perfectly white powder. Color was not measured by an apparatus. Instead, the color change was determined visually.

Example 2

Ten grams (10 g) of WC 9524 (ADM Canadian Plant commercial product), was suspended in 90 grams of water with agitation. NaOH was not exactly measured, but instead was added to the mixture (until a pH higher than 8 was reached) forming a paste-like mixture. Next, $H_2O_2$ was added (not measured) during constant mixing at room temperature to produce a bleached paste-like mixture.

Example 3

Ten grams (10 g) of F7, an experimental wheat dextrin (dark brown), was tested, as in Example 2, to verify whether bleaching was possible with a darker dextrin.

Example 4

Fiber analysis was performed at the ADM Clinton Laboratory on WC 9524 and on the final bleached products from Examples 1-3. Results indicated that the bleached products from Examples 1-3 were very white in color compared to the dark beige color of the original dextrin.

Example 5

WC 9524 (30 grams) was suspended in water (50 grams). 3% NaOH (2.2 grams) was added to the mixture forming a paste-like mixture with a pH 9.1 at 25° C. During the reaction, a total of 143 drops of 3% NaOH was added to maintain the pH. Next, 35 drops of hydrogen peroxide (30-35%) was added to the reaction mixture. After the reaction or color change, the paste-like mixture was oven dried.

Example 6

Dextrin was screened on a 600 micron sieve to remove course particles. The screened dextrin (30 grams) was a corn dextrin called Dextran used in a Fibersol process. The screened dextrin was suspended in water (50 grams). 3% NaOH was added to the mixture forming a paste-like mixture with a pH 9.6. Next, 30 drops of hydrogen peroxide was added and the temperature of the reaction mixture was adjusted to 45° C. for 20 minutes. After the reaction or color change, the paste-like mixture was oven dried overnight at 60° C.

While this invention has been particularly shown and described with references to preferred embodiments thereof, it will be understood by those skilled in the art that various changes in form and details may be made therein without departing from the scope of the invention encompassed by the claims

What is claimed is:

1. A method of forming a bleached dextrin, comprising:
   combining a dextrin-based composition with a caustic agent and an oxidant to form the bleached dextrin;
   wherein the caustic agent is selected from the group consisting of sodium hydroxide, calcium carbonate, sodium carbonate, trisodium phosphate, lime, and combinations of any thereof.

2. The method of claim 1, further comprising heating the bleached dextrin.

3. The method of claim 2, wherein the bleached dextrin is heated to a temperature ranging from 10 to 80° C. for a period of time ranging from 10 to 360 minutes.

4. The method of claim 1, further comprising drying the bleached dextrin.

5. The method of claim 4, wherein the drying occurs at a temperature ranging from 40 to 500° C. for a period of time ranging from 1 to 120 minutes.

6. The method of claim 4, further comprising grinding the bleached dextrin.

7. The method of claim 1, wherein the dextrin-based composition is selected from the group consisting of white dextrins, yellow dextrins, British gums, and combinations of any thereof.

8. The method of claim 1, wherein the dextrin-based composition is selected from the group consisting of a paste, a slurry and a combination thereof.

9. The method of claim 1, wherein the caustic agent is added to the dextrin-based composition in an amount ranging from 0.01% to 10% on dextrin dry basis.

10. The method of claim 1, wherein the oxidant is added to the dextrin-based composition in an amount ranging from 0.1% to 10%.

11. The method of claim 1, wherein the oxidant at a concentration of 0.1 to 70% is added to the dextrin-based composition in an amount ranging from 3 to 15%.

12. The method of claim 1, wherein the bleached dextrin has a whiteness level ranging from 90 to 100% based on CIE Lab model.

13. A method of forming a bleached dextrin, comprising:
    combining a dextrin-based composition selected from the group consisting of maltodextrins, pyrodextrins, and a combination thereof with a caustic agent and an oxidant to form the bleached dextrin;
    wherein the caustic agent is selected from the group consisting of sodium hydroxide, calcium carbonate, sodium carbonate, trisodium phosphate, lime, and combinations of any thereof.

14. The method of claim 13, further comprising heating the bleached dextrin.

15. The method of claim 14, wherein the bleached dextrin is heated to a temperature ranging from 10 to 80° C. for a period of time ranging from 10 to 360 minutes.

16. The method of claim 13, further comprising drying the bleached dextrin.

17. The method of claim 16, wherein the drying occurs at a temperature ranging from 40 to 500° C. for a period of time ranging from 1 to 120 minutes.

18. The method of claim 13, wherein the dextrin-based composition is selected from the group consisting of a paste, a slurry and a combination thereof.

19. The method of claim 13, wherein the caustic agent is added to the dextrin-based composition in an amount ranging from 0.01% to 10% on dextrin dry basis.

20. The method of claim 13, wherein the oxidant is added to the dextrin-based composition in an amount ranging from 0.1% to 10%.

* * * * *